(12) United States Patent
Yamano et al.

(10) Patent No.: US 7,247,732 B2
(45) Date of Patent: Jul. 24, 2007

(54) METHOD FOR PRODUCING OPTICALLY ACTIVE COMPOUND

(75) Inventors: Toru Yamano, Itami (JP); Naohiro Taya, Takarazuka (JP); Akio Ojida, Fukuoka (JP)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

(21) Appl. No.: 11/451,051

(22) Filed: Jun. 12, 2006

(65) Prior Publication Data

US 2006/0229457 A1    Oct. 12, 2006

Related U.S. Application Data

(62) Division of application No. 10/506,309, filed as application No. PCT/JP03/02563 on Mar. 5, 2003, now Pat. No. 7,084,278.

(30) Foreign Application Priority Data

Mar. 6, 2002    (JP)    ............................. 2002-060402

(51) Int. Cl.
    C07D 213/46    (2006.01)
    C07D 233/60    (2006.01)
(52) U.S. Cl. .................................... 546/341; 548/341.5
(58) Field of Classification Search ..................... None
    See application file for complete search history.

(56) References Cited

OTHER PUBLICATIONS

Balan et al., "Selective Formation of α-Methylene-β-amino acid Derivatives through the Aza Version of the Baylis-Millman Reaction," J. Org. Chem. 2001, 66, 6498-6501.*
Andres, J.M., et al., "Enantioselective Reformatsky Reaction Induced by Chiral Beta-Amino Alcohols", Tetrahedron, (1997), vol. 53, No. 10, pp. 3787-3794.
Zhang, Y., et al., "Enantioselective Synthesis of Beta-Hydroxy Esters by Reformatsky Reactions in Chiral Micelles", Tetrahedron: Asymmetry, (1997), vol. 8, No. 21, pp. 3575-3578.
Guette, M., et al., "Synthese Asymetrique De Beta-Hydroxyesters par Reaction De Reformatsky en Presence De (−) Sparteine", Tetrahedron, (1973), vol. 29, pp. 3659-3667.
Pini, D., et al., "New Chiral Ligand for Optically Active Beta-Hydroxy Esters Synthesis by Enantioselective Reformatsky Reactions", Tetrahedron: Asymmetry, (1994), vol. 5, No. 10, pp. 1875-1876.
Soai, K., et al., "Enantioselective Reformatsky Reaction with Ketones. Asymmetric Synthesis of Beta-(tert-Hydroxy)esters", J. Chem. Soc., Chem.Commun., (1993), pp. 811-812.
Andres, J.M., et al., "Synthesis of Chiral alpha, alpha-Difluoro-Beta-Hydroxy Esters by Enantioselective Reformatsky Reaction", Synthesis, (1996), pp. 1070-1072.
Ojida, A., et al., "Highly Enantioselective Reformatsky Reaction of Ketones: Chelation-Assisted Enantioface Discrimination", Organic Letters, (2002), vol. 4, No. 18, pp. 3051-3054.

* cited by examiner

Primary Examiner—Kamal A. Saeed
Assistant Examiner—Andrew B. Freistein

(74) Attorney, Agent, or Firm—Wenderoth, Lind & Ponack, L.L.P.

(57) ABSTRACT

The present invention provides a method for producing an optically active β-hydroxy ester compound represented by the general formula:

$$\text{HO} \overset{R^4 \ R^5}{\underset{R^1 \ R^2}{\overset{*}{\diagdown}\diagup}} CO_2R^3 \quad (III)$$

wherein $R^1$ represents an optionally substituted hydrocarbon group and the like, $R^2$ represents a nitrogen-containing heterocyclic group different from $R^1$, which is represented by the general formula:

$$\diagup\!\!\!\diagdown N \diagdown \quad (V)$$

wherein the ring may be substituted and the like, $R^3$ represents an optionally substituted hydrocarbon group and the like, $R^4$ and $R^5$ represent, the same or different, a hydrogen atom, a halogen atom and the like, the symbol "*" represents an optically active center, which comprises reacting in the presence of a cinchona alkaloid and the like a compound represented by the general formula:

$$R^1 \overset{O}{\underset{}{\diagdown\!\!\!\diagup}} R^2 \quad (I)$$

wherein $R^1$ and $R^2$ are as defined above with a compound represented by the general formula:

$$X \overset{R^4 \ R^5}{\underset{Zn}{\overset{}{\diagdown}\diagup}} CO_2R^3 \quad (II)$$

wherein $R^3$, $R^4$ and $R^5$ are as defined above, and X is a halogen atom.

5 Claims, No Drawings

METHOD FOR PRODUCING OPTICALLY ACTIVE COMPOUND

This application is a divisional of U.S. patent application Ser. No. 10/506,309, which issued as U.S. Pat. No. 7,084,278, which was the National Phase filing of International Patent Application No. PCT/JP03/02563, filed Mar. 5, 2003.

TECHNICAL FIELD

The present invention relates to a method for producing optically active β-hydroxy esters useful in producing pharmaceuticals, agrichemicals, liquid crystals and raw materials therefor.

BACKGROUND ART

In optically active compounds, particularly those used as pharmaceuticals, it is not rare to find that bioactivity, pharmacokinetics, pharmacodynamics, toxicity and the like are different between optical isomers. Therefore, it is required to resolve or separately synthesize optical isomers not only in test and development stages and also in actual production.

An optically active β-hydroxy ester has high versatility as an ingredient for pharmaceuticals or a raw material therefor and, thus, studies on a method for producing it are continued.

A reaction between aldehyde or ketone and a reagent prepared from α-haloester and zinc, a so-called Reformatsky reaction, is extremely useful as a method for producing β-hydroxy esters because of its high versatility. However, such a reaction has not been established as a method for producing optically active compounds. Particularly, high stereoselectivity has not been achieved in a reaction with ketone as described in, for example, *J. Chem. Soc., Chem. Commun.*, 1993, 811; *Tetrahedron*, 1973, 29, 3659; and *Tetrahedron*, 1997, 53 (10), 3787. In addition, a stereoselective Reformatsky reaction using an asymmetric ligand in a reaction with ketone having a heterocyclic ring has never been studied.

If a Reformatsky reaction were proceeded streoselectively, an optically active β-hydroxy ester would be obtained. Since a Reformatsky reaction allows coexisting of functional groups such as ester, amide and the like, it will be a high versatile method. Particularly, since there is no practical method for producing optically active tertiary alcohols which are obtained by a reaction with ketone, a high yield and high versatile method for producing them is desired.

DISCLOSURE OF THE INVENTION

The present inventors made every effort in view of the above situation and, as a result, found that high stereoselectivity can be achieved in the presence of a cinchona alkaloid or a salt thereof when $R^2$ in ketone or aldehyde represented by the general formula (I) is a nitrogen-containing heterocyclic group, which resulted in completion of the present invention.

That is, the present invention relates to:

(1) A method for producing an optically active β-hydroxy ester compound represented by the general formula:

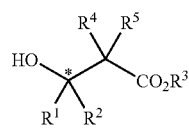

(III)

wherein $R^1$ represents a hydrogen atom, an optionally substituted hydrocarbon group, or an optionally substituted heterocyclic group, $R^2$ represents a nitrogen-containing heterocyclic group different from $R^1$, which is represented by the general formula:

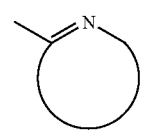

(V)

wherein the ring may be substituted, and may have one or more heteroatoms in addition to the nitrogen atom in the formula, and may have one or more double bonds in addition to the double bond in the formula; or the general formula:

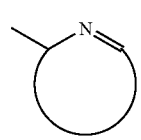

(VI)

wherein the ring may be substituted, and may have one or more heteroatoms in addition to the nitrogen atom in the formula, and may have one or more double bonds in addition to the double bond in the formula, provided that a case is eliminated where $R^1$ is an optionally substituted aromatic group and $R^2$ is a group represented by the general formula:

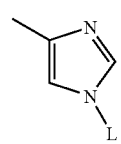

(IV)

wherein L represents a protecting group, $R^3$ represents an optionally substituted hydrocarbon group or an optionally substituted heterocyclic group, $R^4$ and $R^5$ are the same or different, and represent a hydrogen atom, a halogen atom, an optionally substituted silyl group, an optionally substituted hydrocarbon group or an optionally substituted heterocyclic group, and (1) $R^3$ and $R^4$, (2) $R^3$ and $R^5$, or (3) $R^4$ and $R^5$ may be taken together to form a ring, wherein said ring may be substituted, the symbol "*" represents an optically active center, or a salt thereof, which comprises reacting, in the presence of a cinchona alkaloid or a salt thereof, a compound represented by the general formula:

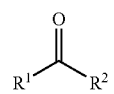

(I)

wherein R¹ and R² are as defined above or a salt thereof with a compound represented by the general formula:

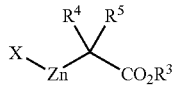

(II)

wherein R³, R⁴ and R⁵ are as defined above, and X is a halogen atom, or a polymer thereof or a salt thereof;

(2) The method according to (1), which further comprises adding a base;

(3) The method according to (2), wherein the base is pyridine;

(4) The method according to (1), wherein the cinchona alkaloid is cinchonine, cinchonidine, quinine, or qunidine;

(5) The method according to (1), wherein R² is an optionally substituted 2-pyridyl group or 4-imidazolyl group; and (6) The method according to (1), wherein R¹ is a hydrogen atom, an optionally substituted aliphatic hydrocarbon group, or an optionally substituted heterocyclic group, and R² is a group different from R¹, which is represented by the general formula:

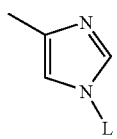

(IV)

wherein L represents a protecting group.

BEST MODE FOR CARRYING OUT THE INVENTION

R¹ in the general formula (I) and R³, R⁴ and R⁵ in the general formula (II) represent a hydrogen atom, an optionally substituted hydrocarbon group, or an optionally substituted heterocyclic group.

For the hydrocarbon group in the "optionally substituted hydrocarbon group" represented by R¹, R³, R⁴ and R⁵, for example, an "aliphatic chain hydrocarbon group", an "alicyclic hydrocarbon group" and an "aromatic hydrocarbon group" may be used.

For the "aliphatic chain hydrocarbon group" representing a hydrocarbon group, for example, a linear- or branched-chain aliphatic hydrocarbon group such as an alkyl group, an alkenyl group, an alkynyl group and the like may be used.

For the "alkyl group", for example, a $C_{1-10}$ alkyl group such as methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methyheptyl, 1-ethylhexyl, n-octyl, 1-methylheptyl, nonyl and the like maybe used. Preferably, a $C_{1-6}$ alkyl group (e.g., methyl, ethyl, n-propyl, isopropyl, n-butyl, sec-butyl, tert-butyl, etc.) and the like may be used.

For the "alkenyl group", for example, a $C_{2-10}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like may be used. Preferably, a $C_{2-6}$ alkenyl group and the like may be used.

For the "alkynyl group", for example, a $C_{2-10}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like may be used. Preferably, a $C_{2-6}$ alkynyl group and the like may be used.

For the "alicyclic hydrocarbon group" representing a hydrocarbon group, for example, a saturated or unsaturated monocyclic or fused polycyclic alicyclic hydrocarbon group such as a cycloalkyl group, a cycloalkenyl group, a cycloalkanedienyl group, a di- or tri-cyclic fused ring of the aforementioned groups and a $C_{6-14}$ aryl group (e.g., benzene etc.) and the like may be used.

For the "cycloalkyl group", for example, a $C_{3-10}$ cycloalkyl group such as cyclopropyl, cyclobutyl, cyclopentyl, cyclohexyl, cycloheptyl cyclooctyl, cyclononyl and the like may be used.

For the "cycloalkenyl group", for example, a $C_{3-10}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl and the like may be used.

For the "cycloalkanedienyl group", for example, a $C_{4-6}$ cycloalkanedienyl group such as 2,4-cyclopentadien-1-yl, 2,4-cyclohexadien-1-yl, 2,5-cyclohexadien-1-yl and the like may be used.

For the "aromatic hydrocarbon group" representing a hydrocarbon group, a monocyclic or fused polycyclic aromatic hydrocarbon group may be used. The aromatic hydrocarbon group is not limited, but is preferably a $C_{6-22}$ aromatic hydrocarbon group, more preferably a $C_{6-18}$ aromatic hydrocarbon group, further preferably a $C_{6-10}$ aromatic hydrocarbon group. Specifically, for example, phenyl, o-tolyl, m-tolyl, p-tolyl, 2,3-xylyl, 2,4-xylyl, mesityl, o-cumenyl, m-cumenyl, p-cumenyl, α-methylbenzyl, benzhydryl, o-biphenyl, m-biphenyl, p-biphenylel, 1-naphthyl, 2-naphthyl, 2-indenyl, 2-anthryl, azurenyl, phenathryl, fluorenyl and the like may be used. Among them, pheyl, 1-naphthyl, 2-naphthyl, 2-anthryl and the like are preferred.

For the aliphatic hydrocarbon group in the "optionally substituted aliphatic hydrocarbon group" represented by R¹, the same groups as those defined above may be used.

For the heterocyclic group in the "optionally substituted heterocyclic group" represented by R¹, R³, R⁴ and R⁵, for example, an aromatic heterocyclic group and a saturated or unsaturated non-aromatic heterocyclic group (an aliphatic heterocyclic group) having one to three kinds (preferably one or two kinds) of at least one (preferably one to four, and more preferably one or two) heteroatoms selected from an oxygen atom, a sulfur atom, a nitrogen atom and the like as an atom constituting the ring (an atom on the ring) may be used. The heterocyclic group is not limited, but is preferably a 5- to 22-membered heterocyclic group, more preferably a 5- to 18-membered heterocyclic group, further preferably a 5- to 14-membered heterocyclic group, and still further preferably a 5- to 10-membered heterocyclic group.

Specifically, examples of the "aromatic heterocyclic group" include a 5- or 6-membered monocyclic aromatic heterocyclic group (e.g., 2-furyl, 3-furyl, 2-thienyl, 3-thienyl, 3-pyrrolyl, 2-oxazolyl, 4-oxazolyl, 5-oxazolyl, 3-isoxazolyl, 4-isoxazolyl, thiazolyl, 3-isothiazolyl, 4-isothiazolyl, 1-imidazolyl, 2-imidazolyl, 4-imidazolyl, 5-imidazolyl, 1-pyrazolyl, 1,2,3-oxadiazolyl, 1,2,4-oxadiazolyl, 1,3,4- oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, 2-pyridyl, 3-pyridyl, 4-pyridyl, 3-pyridazinyl, 2-pyrimidinyl, pyrazinyl, triazinyl, etc.) and a 8- to 12-membered fused aromatic heterocyclic group (e.g., benzofuranyl, isobenzofuranyl, benzothienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.). Preferably, a heterocyclic group in which the above 5- or 6-membered monocyclic aromatic heterocyclic group is fused with a benzene ring or a heterocyclic group in which two same or different heterocyclic rings from the above 5- or 6-membered monocyclic aromatic heterocyclic group are fused may be used.

Specifically, examples of the "non-aromatic heterocyclic group" include a 3- to 8-membered (preferably, 5- or 6-membered) saturated or unsaturated (preferably saturated) non-aromatic heterocyclic group (an aliphatic heterocyclic group) such as pyrrolinyl, imidazolinyl, imidazolidinyl, pyrazolinyl, pyrazolidinyl, quinuclidinyl, aziridinyl, oxiranyl, azetidinyl, pyrrolidinyl, tetrahydrofuryl, thiolanyl, piperidino, 2-piperidyl, 3-piperidyl, 4-piperidyl, tetrahydropyranyl, 2-dioxolanyl, 2-thiazanyl, 3-thiazanyl, 2-morpholinyl, 3-morpholinyl, thiomorpholinyl, 2-piperazinyl and the like may be used.

$R^2$ represents a nitrogen-containing heterocyclic group different from $R^1$, which is represented by the general formula (V):

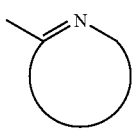
(V)

wherein the ring may be substituted, and may have one or more heteroatoms in addition to the nitrogen atom in the formula, and may have one or more double bonds in addition to the double bond in the formula; or the general formula (VI):

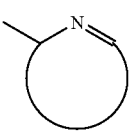
(VI)

wherein the ring may be substituted, and may have one or more heteroatoms in addition to the nitrogen atom in the formula, and may have one or more double bonds in addition to the double bond in the formula.

The nitrogen-containing heterocyclic ring represented by the general formula (V) or (VI) may contain one to three kinds (preferably one or two kinds) of one or more. (preferably one to four, more preferably one or two) heteroatoms selected from an oxygen atom, a sulfur atom, a nitrogen atom and the like in addition to the nitrogen atom in the formula, and may have one or more double bonds in addition to the double bond in the formula. For the substituent which the nitrogen-containing heterocyclic group represented by the general formula (V) or (VI) may have, the same number of the same group as the substituent in an "optionally substituted heterocyclic group" defined below may be used.

Specifically, as the nitrogen-containing heterocyclic ring represented by the general formula (V) or (VI), a 5- or 6-membered monocyclic nitrogen-containing aromatic heterocyclic group such as 3H-pyrrol-2-yl, 2H-pyrrol-5-yl, 2H-pyrrol-2-yl, 3H-pyrrol-5-yl, 1H-imidazol-4-yl, 4H-imidazol-4-yl, 2H-imidazol-4-yl, 4H-imidazol-5-yl, 4H-imidazol-2-yl, 1H-imidazol-2-yl, 1H-imidazol-3-yl, 2H-imidazol-2-yl, 4H-imidazol-2-yl, 3-oxazol-4-yl, 1,3-oxazol-2-yl, isoxazol-3-yl, 1H-pyrazol-3-yl, 3H-pyrazol-5-yl, 4H-pyrazol-3-yl, 1,3,4-oxadiazol-2-yl, 1,2,5-oxadiazol-3-yl, 1,2,4-oxadiazol-5-yl, 1,2,3-oxadiazol-4-yl, 1,2,4-oxadiazol-3-yl, 1,3,4-thiadiazol-2-yl, 1,2,5-thiadiazol-3-yl, 1,2,4-thiadiazol-5-yl, 1,2,3-thiadiazol-4-yl, 1,2,4-thiadiazol-3-yl, 1,3-thiazol-4-yl, 1,3-thiazol-2-yl, isothiazol-3-yl, 1H-1,2,3-triazol-4-yl, 3H-1,2,4-triazol-5-yl, 3H-1,2,4-triazol-3-yl, 2H-tetrazol-2-yl, 2H-tetrazol-5-yl, 1H-tetrazol-5-yl, 2-pyridyl, pyridazin-3-yl, pyrimidin-4-yl, pyrimidin-2-yl, pyrazin-2-yl, 1,2,3-triazin-4-yl, 1,3,5-triazin-2-yl, 1,2,4-triazin-6-yl, 1,2,4-triazin-5-yl, 1,2,4-triazin-3-yl and the like and a 8- to 12-membered fused nitrogen-containing aromatic heterocyclic group such as 3H-indol-2-yl, 2H-isoindol-2-yl, 2H-isoindol-1-yl, quinolin-2-yl, isoquinolin-1-yl, isoquinolin-3-yl, 7H-purin-8-yl, 9H-purin-8-yl, 7H-purin-6-yl, 9H-purin-6-yl, 9H-purin-2-yl, 7H-purin-2-yl, 1H-indazol-3-yl, quinazolin-2-yl, quinazolin-4-yl, cinnolin-3-yl, quinoxalin-2-yl, phthalazin-1-yl, pteridin-2-yl, pteridin-4-yl, pteridin-6-yl, pteridin-7-yl, 7H-imidazo[4,5-c]pyridazin-3-yl, 5H-imidazo[4,5-c]pyridazin-3-yl, 7H-imidazo[4,5-c]pyridazin-6-yl, 5H-imidazo[4,5-c]pyridazin-6-yl, 1H-pyrazolo[3,4-b]pyridin-6-yl, 3H-pyrazolo[3,4-b]pyridin-6-yl, 3H-pyrazolo[3,4-b]pyridin-3-yl, 1,3-benzoxazol-2-yl, 1,2-benzoxazol-3-yl, 1,3-benzothiazol-2-yl, 1,2-benzothiazol-3-yl, 1H-1,2,3-benzotriazol-1-yl, 3H-imidazo[4,5-b]pyridin-2-yl, 1H-imidazo[4,5-b]pyridin-2-yl, 3H-imidazo[4,5-b]pyridin-5-yl, 1H-imidazo[4,5-b]pyridin-5-yl, 3H-imidazo[4,5-c]pyridin-2-yl, 1H-imidazo[4,5-c]pyridin-2-yl, 3H-imidazo[4,5-c]pyridin-4-yl, 1H-imidazo[4,5-c]pyridin-4-yl, 3H-imidazo[4,5-c]pyridin-6-yl, 1H-imidazo[4,5-c]pyridin-6-yl, phenanthridin-6-yl may be used. A heterocyclic ring in which the above 5- or 6-membered monocyclic nitrogen-containing aromatic heterocyclic group is fused with a benzene ring and a heterocyclic group in which two same or different heterocyclic rings from the above 5- or 6-membered monocyclic nitrogen-containing aromatic heterocyclic group are fused are also preferred. Further, for example, a 3- to 8-membered (preferably 5- or 6-membered) unsaturated nitrogen-containing aliphatic heterocyclic group such as 3,4-dihydro-2H-pyrrol-5-yl, 3,4-dihydro-2H-pyrrol-2-yl, 4,5-dihydro-1H-imidazol-4-yl, 2,5-dihydro-1H-imidazol-4-yl, 2,5-dihydro-1H-imidazol-2-yl, 4,5-dihydro-1H-imidazol-2-yl, 4,5-dihydro-1H-pyrazol-3-yl, 4,5-dihydro-3H-pyrazol-3-yl, 2,5-dihydro-1,3-thiazol-2-yl, 4,5-dihydro-1,3-thiazol-2-yl, 2,5-dihydro-1,3-thiazol-4-yl, 4,5-dihydro-1,3-thiazol-4-yl, 4,5-dihydro-1,3-thiazol-3-yl, 2,5-dihydro-1,3-oxazol-2-yl, 4,5-dihydro-1,3-oxazol-2-yl, 2,5-dihydro-1,3-oxazol-4-yl, 4,5-dihydro-1,3-oxazol-4-yl, 4,5-dihydro-1,3-oxazol-3-yl and the like may be used.

The halogen atom represented by X, $R^4$ and $R^5$ are chlorine, bromine or iodine, and bromine and iodine are preferred.

Herein, for the ring in a phrase "(1) $R^3$ and $R^4$, (2) $R^3$ and $R^5$, or (3) $R^4$ and $R^5$ may be taken together to form a ring, wherein said ring may be substituted", an "alicyclic hydrocarbon", an "aromatic hydrocarbon", a "heterocyclic ring such as an aromatic heterocyclic ring and a non-aromatic heterocyclic ring" and the like may be used.

For the "alicyclic hydrocarbon", for example, a saturated or unsaturated monocyclic or fused polycyclic alicyclic hydrocarbon such as cycloalkane, cycloalkene, cycloalkanediene, and a di- or tri-cyclic fused ring of the aforementioned groups and a $C_{6-14}$ aryl (e.g., benzene etc.) may be used.

For the "cycloalkane", for example, $C_{3-10}$ cycloalkane such as cyclopropane, cyclobutane, cyclopentane, cyclohexane, cycloheptane, cyclooctane, cyclononane and the like may be used.

For the "cycloalkene", for example, $C_{3-10}$ cycloalkene such as cyclopentene, cyclohexene, cyclobuten and the like may be used.

For the "cycloalkanediene", for example, $C_{4-6}$ cycloalkanediene such as cyclopentadiene, cyclohexadiene, cyclohexanediene and the like may be used.

For the "aromatic hydrocarbon", a monocyclic or fused polycyclic aromatic hydrocarbon may be used without any limitation. Preferably a $C_{6-22}$ aromatic hydrocarbon, more preferably a $C_{6-18}$ aromatic hydrocarbon, and further preferably a $C_{6-10}$ aromatic hydrocarbon may be used. Specifically, examples of the aromatic hydrocarbon include benzene, toluene, xylene, mesitylene, cumene, styrene, 1,2,3-trimethylbenzene, pentalene, indene, naphthalene, azulene, heptalene, biphenylene, benzocyclohepten, as-indacene, s-indacene, acenaphthylene, fluorene, phenalene, phenanthrene, anthracene, fluoranthene, acephenanthrylene, aceanthrylene, triphenylene, pyrene, chrysene, naphthacene and the like. Among them, benzene, toluene, naphthalene and the like are preferred.

For the "heterocyclic ring", for example, an aromatic heterocyclic ring and a saturated or unsaturated non-aromatic heterocyclic ring (an aliphatic heterocyclic ring) having one to three kinds (preferably one or two kinds) of at least one (preferably one to four, and more preferably one or two) heteroatoms selected from an oxygen atom, a sulfur atom, a nitrogen atom and the like as an atom constituting the ring (an atom on the ring) may be used. The heterocyclic ring is not limited, but is preferably a 5- to 22-membered heterocyclic ring, more preferably a 5- to 18-membered heterocyclic ring, further preferably a 5- to 14-membered heterocyclic ring, and still further preferably a 5- to 10-membered heterocyclic ring.

Specifically, examples of the "aromatic heterocyclic ring" include a 5- or 6-membered monocyclic aromatic heterocyclic ring (e.g., furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine, etc.) and a 8- to 12-membered fused aromatic heterocyclic ring (e.g., benzofuran, isobenzofuran, benzothiophene, indole, isoindole, indazole, benzindazole, benzoxazole, 1,2-benzisoxazole, benzothiazole, benzopyran, 1,2-benzisothiazole, 1H-benzotriazole, quinoline, isoquinoline, cinnoline, quinazoline, quinoxaline, phthalazine, naphthyridine, purine, pteridine, carbazole, α-carboline, β-carboline, γ-carboline, acridine, phenoxazine, phenothiazine, phenazine, phenoxathiine, thianthrene, phenanthridine, phenanthroline, indolizine, pyrrolo[1,2-b]pyridazine, pyrazolo[1,5-a]pyridine, imidazo[1,2-a]pyridine, imidazo[1,5-a]pyridine, imidazo[1,2-b]pyridazine, imidazo[1,2-a]pyrimidine, 1,2,4-triazolo[4,3-a]pyridine, 1,2,4-triazolo[4,3-b]pyridazine, etc.) may be used. Preferably, a heterocyclic group in which the above 5- or 6-membered monocyclic aromatic heterocyclic group is fused with a benzene ring and a heterocyclic group in which two same or different heterocyclic rings from the above 5- or 6-membered monocyclic aromatic heterocyclic group are fused may be used.

Specifically, examples of the "non-aromatic heterocyclic ring" include a 3- to 8-membered (preferably, 5- or 6-membered) saturated or unsaturated (preferably saturated) non-aromatic heterocyclic ring (an aliphatic heterocyclic ring) such as pyrroline, imidazoline, imidazolidine, pyrazoline, pyrazolidine, quinuclidine, aziridine, oxirane, azetidine, pyrrolidine, tetrahydrofuran, thiolane, piperidine, tetrahydropyran, dioxolane, thiazane, morpholine, thiomorpholine, piperazine and the like.

The cinchona alkaloid is, for example, cinchonine, cinchonidine, quinine, or quinidine.

In the present invention, examples of the substituent from the "optionally substituted hydrocarbon group", the "optionally substituted heterocyclic group", the "optionally substituted aromatic group", the "optionally substituted aliphatic hydrocarbon group", a phrase "(1) $R^3$ and $R^4$, (2) $R^3$ and $R^5$, or (3) $R^4$ and $R^5$ may be taken together to form a ring, wherein said ring may be substituted" or a phrase "the ring may be substituted, and may have one or more heteroatoms in addition to the nitrogen atom in the formula, and may have one or more double bonds in addition to the double bond in the formula" include but are not limited to (i) an optionally substituted alkyl group; (ii) an optionally substituted alkenyl group; (iii) an optionally substituted alkynyl group; (iv) an optionally substituted aryl group; (v) an optionally substituted aralkyl group; (vi) an optionally substituted cycloalkyl group; (vii) an optionally substituted cycloalkenyl group; (viii) an optionally substituted heterocyclic group; (ix) an optionally substituted amino group; (x) an optionally substituted hydroxyl group; (xi) an optionally substituted thiol group; (xii) an optionally substituted alkyl sulfinyl group; (xiii) an optionally esterified or amidated carboxyl group; (xiv) an optionally substituted thiocarbamoyl group; (xv) an optionally substituted sulfamoyl group; (xvi) a halogen atom (e.g., fluorine, chlorine, bromine, iodine, etc., and preferably chlorine, bromine, etc.); (xvii) a cyano group; (xviii) an isocyano group; (xix) a cyanate group; (xx) an isocyanate group; (xxi) a thiocyanate group; (xxii) an isothiocyanate group; (xxiii) a nitro group; (xxiv) a nitroso group; (xxv) an acyl group derived from sulfonic acid; and the like. These optional substituents may bind to one to five, preferably one to three replaceable positions. Additionally, when there are two or more substituents, they may be the same or different from each other.

For the alkyl group in the "optionally substituted alkyl group" as the substituent, for example, $C_{1-6}$ alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl and the like may be used. Examples of the substituent of the alkyl group include a lower alkoxyl group (e.g., $C_{1-6}$ alkoxy such as methoxy, ethoxy, propoxy, etc.), a halogen atom (e.g., fluorine, chlorine, bromine, iodine, etc.), a lower alkyl group (e.g., $C_{1-6}$ alkyl such as methyl, ethyl, propyl, etc.), a lower alkenyl group (e.g., $C_{2-6}$ alkenyl such as vinyl, allyl, etc.), a lower alkynyl group (e.g., $C_{2-6}$ alkynyl such as ethynyl, propargyl, etc.), an optionally substituted amino group, an optionally substituted hydroxyl group, a cyano group, an optionally substituted amidino group, a carboxyl group, a lower alkoxycarbonyl group (e.g., $C_{1-6}$ alkoxycarbonyl such as methoxycarbonyl, ethoxycarbonyl, etc.), an optionally substituted carbamoyl group (e.g., methylcarbamoyl etc.), a 5- or 6-membered monocyclic aromatic heterocyclic group (e.g., pyridyl etc.) and the like. These optional substituents may bind to one to three replaceable positions.

For the "optionally substituted amino group", the "optionally substituted hydroxyl group" and the "optionally substituted amidino group" as a substituent for the "optionally substituted alkyl group", the same group as an "optionally substituted amino group", an "optionally substituted hydroxyl group" and an "optionally substituted amidino group" as a substituent for an "optionally substituted aromatic ring or heterocyclic ring" mentioned below may be used.

For the alkenyl group in the "optionally substituted alkenyl group" as a substituent, for example, $C_{2-6}$ alkenyl such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like may be used. For the substituent in the alkenyl group, the same number of the same group as the substituent in the "optionally substituted alkyl group" as a substituent may be used.

For the alkynyl group in the above "optionally substituted alkynyl group" as a substituent, for example, $C_{2-6}$ alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like may be used. For the substituent in the alkynyl group, the same number of the same group as the substituent in the "optionally substituted alkyl group" as a substituent may be used.

For the aryl group in the "optionally substituted aryl group" as a substituent, for example, $C_{6-14}$ aryl such as phenyl, naphthyl, anthryl, phenanthryl, acenaphthyrenyl and the like may be used. For the substituent in the aryl group, the same number of the same group as the substituent in the "optionally substituted alkyl group" as a substituent may be used.

For the aralkyl group in the "optionally substituted aralkyl group" as a substituent, for example, $C_{7-11}$ aralkyl such as benzyl, phenethyl, naphthylmethyl and the like may be used. For the substituent in the aralkyl group, the same number of the same group as the substituent in the "optionally substituted alkyl group" as a substituent may be used.

For the cycloalkyl group in the "optionally substituted cycloalkyl group" as a substituent, for example, $C_{3-7}$ cycloalkyl such as cyclopropyl, cyclobutyl, cyclopentyl, cyclohexyl, cycloheptyl and the like may be used. For the substituent in the cycloalkyl group, the same number of the same group as the substituent in the "optionally substituted alkyl group" as a substituent may be used.

For the cycloalkenyl group in the "optionally substituted cycloalkenyl group" as a substituent, for example, $C_{3-7}$ cycloalkenyl such as cyclopropenyl, cyclobutenyl, cyclopentenyl, cyclohexenyl and the like may be used. For the substituent in the cycloalkenyl group, the same number of the same group as the substituent in the "optionally substituted alkyl group" as a substituent may be used.

For the heterocyclic group in the "optionally substituted heterocyclic group" as a substituent, for example, an aromatic heterocyclic group and a saturated or unsaturated non-aromatic heterocyclic group (an aliphatic heterocyclic group) having one to three kinds (preferably one or two kinds) of at least one (preferably one to four, and more preferably one or two) heteroatoms selected from an oxygen atom, a sulfur atom, a nitrogen atom and the like as an atom constituting the ring (an atom on the ring) may be used.

For the "aromatic heterocyclic group", a 5- or 6-membered monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like and a 8- to 12-membered fused polycyclic aromatic heterocyclic group such as benzofuranyl, isobenzofuranyl, benzo[b]thienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like may be used.

For the "non-aromatic heterocyclic group", a 3- to 8-membered (preferably, 5- or 6-membered) saturated or unsaturated (preferably saturated) non-aromatic heterocyclic group (an aliphatic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl and the like or a non-aromatic heterocyclic group in which a part or all of double bonds in the above monocyclic aromatic heterocyclic group or fused polycyclic aromatic heterocyclic group are saturated such as 1,2,3,4-tetrahydroquinolyl, 1,2,3,4-tetrahydroisoquinolyl and the like may be used.

For the substituent which the "optionally substituted heterocyclic group" as a substituent may have, a lower alkyl group (e.g., $C_{1-6}$ alkyl such as methyl, ethyl, propyl, etc.), a lower alkenyl group (e.g., $C_{2-6}$ alkenyl such as vinyl, allyl, etc.), a lower alkynyl group (e.g., $C_{2-6}$ alkynyl such as ethynyl, propargyl, etc.), an optionally substituted amino group, an optionally substituted hydroxyl group, a halogen atom (e.g., fluorine, chlorine, bromine), an optionally substituted imidoyl group, an optionally substituted amidino group and the like may be used. These optional substituents may bind to one to five, preferably one to three replaceable positions.

For the "optionally substituted amino group", the "optionally substituted hydroxyl group" and the "optionally substituted amidino group" which the "optionally substituted heterocyclic group" as a substituent may have, the same group as an "optionally substituted amino group", an "optionally substituted hydroxyl group", an "optionally substituted imidoyl group" and an "optionally substituted amidino group" as a substituent in an "optionally substituted aromatic homocyclic or heterocyclic group" mentioned below may be used.

For the substituent in the "optionally substituted amino group", the "optionally substituted amidino group", the "optionally substituted hydroxyl group" and the "optionally substituted thiol group" as a substituent, for example, a lower alkyl group (e.g., $C_{1-6}$ alkyl such as methyl, ethyl, propyl, isopropyl, butyl, isobutyl, tert-butyl, pentyl, hexyl, etc.) which may be substituted with a substituent selected from a halogen atom (e.g., fluorine, chlorine, bromine, etc.), optionally halogenated $C_{1-6}$ alkoxy (e.g., methoxy, ethoxy, trifluoromethoxy, 2,2,2-trifluoroethoxy, trichloromethoxy, 2,2,2-trichloroethoxy, etc.) and a $C_{7-11}$ alkylaryl group (e.g., o-toluyl, m-toluyl, p-toluyl, xylyl, mesityl, etc., preferably $C_{1-5}$ alkylphenyl etc.); an acyl group ($C_{1-6}$ alkanoyl (e.g., formyl, acetyl, propionyl, pivaloyl, etc.), benzoyl, $C_{1-6}$ alkylsulfonyl (e.g., methanesulfonyl etc.), benzenesulfonyl, etc.); an optionally halogenated $C_{1-6}$ alkoxycarbonyl group (e.g., methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl, etc.); a $C_{1-6}$ alkoxycarbonyl group which may be substituted with a phenyl group (e.g., benzyloxycarbonyl etc.); aryl (e.g., $C_{6-10}$ aryl such as phenyl, 1-naphthyl, 2-naphthyl, etc.); aralkyl (e.g., $C_{7-10}$ aralkyl such as benzyl, phenethyl, etc., preferably phenyl-$C_{1-4}$ alkyl etc.); arylalkenyl (e.g., $C_{8-10}$ arylalkenyl such as cinnamyl etc., preferably phenyl-$C_{2-4}$ alkenyl etc.) and a heterocyclic group (the same group as the heterocyclic group in the "optionally substituted heterocyclic group" as a substituent may be used, and these optional substituents may bind to one to three replaceable positions.) may be used.

The "amino group" in the "optionally substituted amino group" as a substituent may be substituted with one or two $C_{1-6}$ alkyl groups. These optional substituents may bind to one or two replaceable positions. In addition, two substituents may be taken together with a nitrogen atom to form a cyclic amino group. As such acyclic amino group, for example, a 3- to 8-membered (preferably 5- or 6-membered) cyclic amino group such as 1-azetidinyl; 1-pyrrolidinyl; piperidino; thiomorpholino; morpholino; 1-piperazinyl which may have lower alkyl (e.g., $C_{1-6}$ alkyl such as methyl, ethyl, propyl, isopropyl, butyl, tert-butyl, pentyl, hexyl, etc.), aralkyl (e.g., $C_{7-10}$ aralkyl such as benzyl, phenethyl, etc.), or aryl (e.g., $C_{6-10}$ aryl such as phenyl, 1-naphthyl, 2-naphthyl, etc.) at the 4-position; 1-pyrrolyl; 1-imidazolyl and the like may be used.

For the alkylsulfinyl group in the "optionally substituted alkylsulfinyl group" as a substituent, $C_{1-6}$ alkylsulfinyl such as methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, hexylsulfinyl and the like may be used. For the substituent in the alkylsulfinyl, the same number of the same group as the substituent in the "optionally substituted alkyl group" as a substituent may be used.

For the "optionally esterified or amidated carboxyl group" as a substituent, a carboxyl group, alkoxycarbonyl, aryloxycarbonyl, aralkyloxycarbonyl, carbamoyl, N-monosubstituted carbamoyl and N,N-disubstituted carbamoyl may be used.

For the "alkoxycarbonyl", for example, $C_{1-6}$ alkoxycarbonyl (lower alkoxycarbonyl) such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and the like may be used. Among them, $C_{1-3}$ alkoxycarbonyl such as methoxycarbonyl, ethoxycarbonyl, propoxycarbonyl and the like are preferred. The "lower alkoxycarbonyl" may have a substituent and, for the substituent, a hydroxyl group; an optionally substituted amino group [the amino group may have one or two substituents such as a lower alkyl group (e.g., $C_{1-6}$ alkyl such as methyl, ethyl, propyl, isopropyl, butyl, isobutyl, tert-butyl, pentyl, hexyl, etc., preferably methyl, ethyl, etc.) which may be substituted with one to five halogen atoms (e.g., fluorine, chlorine, bromine, iodine, etc.); an acyl group (e.g., $C_{1-6}$ alkanoyl such as formyl, acetyl, propionyl, pivaloyl, etc.; benzoyl etc.); a carboxyl group; $C_{1-6}$ alkoxycarbonyl; etc.]; a halogen atom (e.g., fluorine, chlorine, bromine, etc.); a nitro group; a cyano group; a lower alkoxyl group (e.g., $C_{1-6}$ alkoxy such as methoxy, ethoxy, n-propoxy, isopropoxy, n-butoxy, isobutoxy, sec-butoxy, tert-butoxy, etc., preferably methoxy, ethoxy, etc.) which may be substituted with one to five halogen atoms (e.g., fluorine, chlorine, bromine, iodine, etc.) may be used. These substituents are the same or different and, preferably, one, two or three (preferably one or two) of them bind to.

For the "aryloxycarbonyl", for example, $C_{6-14}$ aryloxycarbonyl such as phenoxycarbonyl, 1-naphthoxycarbonyl, 2-naphthoxycarbonyl, 1-phenanthoxycarbonyl and the like are preferred. The "aryloxycarbonyl" may have a substituent and, for the substituent, the same number of the same group as the substituent in the "alkoxycarbonyl" as a substituent may be used.

For the "aralkyloxycarbonyl", for example, $C_{7-14}$ aralkyloxycarbonyl (preferably $C_{6-10}$ aryl-$C_{1-4}$ alkoxy-carbonyl etc.) such as benzyloxycarbonyl, phenethyloxycarbonyl and the like are preferred. The "aralkyloxycarbonyl", may have a substituent and, for the substituent, the same number of the same group as the substituent in the "alkoxycarbonyl" as a substituent may be used.

The "N-monosubstituted carbamoyl" means a carbamoyl group which has one substituent on a nitrogen atom and, for the substituent, for example, lower alkyl (e.g., $C_{1-6}$ alkyl such as methyl, ethyl, propyl, isopropyl, butyl, isobutyl, tert-butyl, pentyl, hexyl, etc.); lower alkenyl (e.g., $C_{2-6}$ alkenyl such as vinyl, allyl, isopropenyl, propenyl, butenyl, pentenyl, hexenyl, etc.); cycloalkyl (e.g., $C_{3-6}$ cycloalkyl such as cyclopropyl, cyclobutyl, cyclopentyl, cyclohexyl, etc.); aryl (e.g., $C_{6-10}$ aryl such as phenyl, 1-naphthyl, 2-naphthyl, etc.); aralkyl (e.g., $C_{7-10}$ aralkyl such as benzyl, phenethyl, etc., preferably phenyl-$C_{1-4}$ alkyl etc.); arylalkenyl (e.g., $C_{8-10}$ arylalkenyl such as cinnamyl etc., preferably phenyl-$C_{2-4}$ alkenyl etc.); a heterocyclic group (e.g., the same group as the "heterocyclic group" in the "optionally substituted heterocyclic group" as a substituent etc.) and the like may be used. The lower alkyl, the lower alkenyl, the cycloalkyl, the aryl, the aralkyl, the arylalkenyl and the heterocyclic group may have a substituent and, for the substituent, the same number of the same group as the substituent in the alkoxycarbonyl as a substituent may be used.

The "N,N-disubstituted carbamoyl" means a carbamoyl group which has two substituents on a nitrogen atom, as an example of one substituent, the same group as the substituent in the "N-monosubstituted carbamoyl" as a substituent may be used and, as an example for the other substituent, for example, lower alkyl (e.g., $C_{1-6}$ alkyl such as methyl, ethyl, propyl, isopropyl, butyl, tert-butyl, pentyl, hexyl, etc.), $C_{3-7}$ cycloalkyl (e.g., cyclopropyl, cyclobutyl, cyclopentyl, cyclohexyl, etc.), $C_{7-10}$ aralkyl (e.g., benzyl, phenethyl, etc., preferably phenyl-$C_{1-4}$ alkyl etc.) and the like maybe used. In addition, two substituents may be taken together with a nitrogen atom to form a cyclic amino group. As such cyclic aminocarbamoyl, for example, a 3- to 8-membered (preferably 5- or 6-membered) cyclic aminocarbonyl such as 1-azetidinylcarbonyl; 1-pyrrolidinylcarbonyl; piperidinocarbonyl; morpholinocarbonyl; 1-piperazinylcarbonyl; and 1-piperazinylcarbonyl which may have lower alkyl (e.g., $C_{1-6}$ alkyl such as methyl, ethyl, propyl, isopropyl, butyl, tert-butyl, pentyl, hexyl, etc.), aralkyl (e.g., $C_{7-10}$ aralkyl such as benzyl, phenethyl, etc.), or aryl (e.g., $C_{6-10}$ aryl such as phenyl, 1-naphthyl, 2-naphthyl, etc.) at the 4-position may be used.

For the substituent in the "optionally substituted thiocarbamoyl group" and the "optionally substituted sulfamoyl group" as a substituent, the same group as the substituent for the "N-monosubstituted carbamoyl" and the "N,N-disubstituted carbamoyl" in the "optionally esterified or amidated carboxyl group" as a substituent may be used.

For the "acyl derived from sulfonic acid" as a substituent, for example, a group in which one substituent on the nitrogen atom in the N-monosubstituted carbamoyl is coupled with sulfonyl may be used and, preferably acyl derived from $C_{1-6}$ alkylsulfonyl such as methanesulfonyl, ethanesulfonyl and the like may be used.

For the substituent in the "optionally substituted silyl group" represented by $R^4$ and $R^5$, the same number of the same group as the substituent in the "optionally substituted alkyl group" as a substituent may be used. Specifically, for example, a trimethylsilyl group, a tert-butyldimethylsilyl group, a tert-butyldiphenylsilyl group, a triphenylsilyl group and the like may be used.

The symbol "*" represents herein an optically active center (a chiral center).

$R^1$ and $R^2$ are as defined above, provided that a case is eliminated from the present invention where $R^1$ is an optionally substituted aromatic group and $R^2$ is a group represented by the general formula (IV):

wherein L represents a protecting group.

The "optionally substituted aromatic group" represented by $R^1$ is a monocyclic or fused bicyclic aromatic group which may be substituted with one or more substituents. Specifically, examples include phenyl, 1-naphthyl, 2-naphthyl, 2-indenyl, 2-anthryl, azulenyl, phenanthryl, phenalenyl, fluorenyl, indacenyl, biphenylenyl, heptalenyl, acenaphthylenyl and the like. Among them, phenyl, 1-naphthyl, 2-naphthyl, 1-anthryl and 2-anthryl are preferred. For the substituent, the same number of the same group as the substituent in the "optionally substituted aryl group" as a substituent may be used.

The protecting group represented by L is a protecting group for an amino acid and, specifically, examples include formyl, and $C_{7-10}$ aralkyloxymethyl (benzyloxymethyl etc.), $C_{1-6}$ alkylcarbonyloxymethyl (tert-butylcarbonyloxymethyl etc.), $C_{6-12}$ arylsulfonyl (p-toluensulfonyl etc.), and di-$C_{1-4}$ alkylaminosulfonyl, and trityl, each of which maybe substituted. As the substituent for them, a halogen atom (fluorine, chlorine, bromine, iodine), $C_{1-6}$ alkyl-carbonyl (acetyl, propionyl, valeryl, etc.), and a nitro group may be used. The number of the substituents is one to three.

For $R^2$, particularly, optionally substituted 2-pyridyl or optionally substituted 4-imidazolyl (wherein for the substituents, the same number of the same group as the substituent which the "optionally substituted heterocyclic group" as a substituent may have may be used) are preferred, and particularly 2-pyridyl and 4-imidazolyl are preferred.

For $R^3$, particularly methyl, ethyl tert-butyl, menthyl and the like are preferred.

For $R^4$, particularly hydrogen, fluorine, bromine, methyl, ethyl, propyl, butyl, benzyl and the like are preferred.

For $R^5$, particularly hydrogen, fluorine, bromine, methyl, ethyl, propyl, butyl, benzyl and the like are preferred.

The method according to the present invention can be carried out as described below.

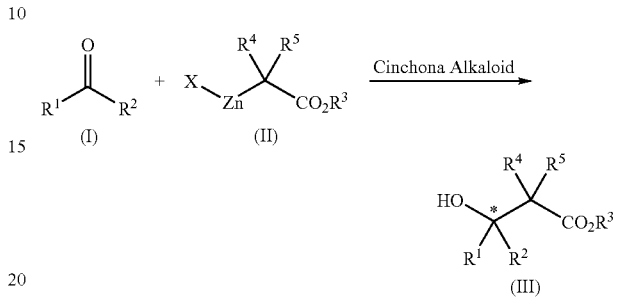

wherein each symbol is as defined above.

The compound represented by the general formula (II) may be produced by reacting α-haloester and zinc according to a method described in, for example, *Jikken Kagaku Kouza*, vol. 25, 4th ed., p. 72, Chem. Soc. Japan, Maruzen, 1992. Powder-, flake-, and wool-like zinc may be used. These can be activated by diluted hydrochloric acid treatment and the like prior to use. Further, trimethylsilyl chloride or dibromoethane may be added at a catalytic amount.

A reaction of the compound represented by the general formula (I) and the compound represented by the general formula (II) is generally carried out in a solvent.

Any solvent may be used as far as it does not affect the reaction and, for example, a hydrocarbon solvent (e.g., hexane, pentane, cyclohexane), an amide solvent (e.g., N,N-dimethylformamide, N,N-dimethylacetamide, N-methylpyrrolidone), an aromatic hydrocarbon solvent (e.g., toluene, benzene), analiphatic ester solvent (e.g., ethyl acetate, propyl acetate), an ether solvent (e.g., diehtyl ether, diisopropyl ether, tetrahydrofuran, 1,4-dioxane, 1,2-dimethoxyethane), a halogenated hydrocarbon solvent (e.g., chloroform, dichloromethane, 1,2-dichloroethane) and the like may be used. These solvents maybe used alone or mixed in any combination thereof. Particularly, tetrahydrofuran, diethyl ether, benzene and toluene are preferred. An amount of the solvent to be used is generally about 1 to about 1000 parts by volume, preferably about 5 to about 100 parts by volume relative to an amount of the compound represented by the general formula (I).

A reaction temperature is about –100° C. to about 100° C., preferably about –50° C. to about 50° C.

A reaction time is not limited, but is 1 minute to 50 hours, preferably 10 minutes to 10 hours.

An amount of the compound represented by the general formula (II) to be used is about 0.5 to about 10 equivalents, preferably about 1 to about 10 equivalents relative to an amount of the compound represented by the general formula (I).

The cinchona alkaloid is, for example, cinchonine, cinchonidine, quinine, or quinidine. An amount to be used is about 0.5 to about 10 equivalents, preferably about 1 to about 3 equivalents, more preferably about 1 to about 2 equivalents relative to an amount of the compound represented by the general formula (I).

In the method of the present invention, addition of a base improves yield and stereoselectivity in some cases. As the base, an organic base is preferably used. Examples of the organic base include but are not limited to triethylamine, trimethylamine, diisopropylethylamine, pyridine, picoline, dimethylaminopyridine, ethanolamine, diethanolamine, dicyclohexylamine, quinoline and the like. Preferably diisopropylethylamine, quinoline and pyridine, more preferably diisopropylethylamine and pyridine, further preferably pyridine may be used.

An amount of the base to be used is about 0.1 to about 10 equivalents, preferably about 0.5 to about 5 equivalents, more preferably about 1 to about 4 equivalents relative to an amount of the compound represented by the general formula (I).

Timing for adding the base into the reaction system is not limited, but the base may be added at any time as far as it does not affect the reaction. Preferably, the base is added after the compound represented by the general formula (II) and the cinchona alkaloid are mixed into the reaction solvent. More preferably, the base is added 1 minute to 30 minutes after mixing of the compound represented by the general formula (II) and the cinchona alkaloid into the reaction solvent.

The optically active β-hydroxy ester represented by the general formula (III) thus obtained may be further isolated and purified by using the known method such as solvent extraction, solvent exchange, re-dissolution into another solvent, salting out, crystallization, recrystallization, chromatography and the like.

The compound represented by the general formula (I), (II) or (III) may form a salt thereof. The salt of the compound is not limited as far as it does not affect the reaction. For example, a salt with an inorganic base, an ammonium salt, a salt with an organic base, a salt with an inorganic acid, a salt with an organic acid and a salt with an amino acid may be used. Preferable examples of the salt with an inorganic base include an alkali metal salt such as a sodium salt, a potassium salt and the like; an alkaline earth metal salt such as a calcium salt, a magnesium salt and the like; an aluminum salt; an ammonium salt; and the like. Preferable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with an inorganic acid include salts with hydrochloric acid, hydrobromic acid, nitric acid, sulfuric acid, phosphoric acid and the like. Preferable examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with a basic amino acid include salts with arginine, lysine, ornithine and the like. Preferable examples of the salt with an acidic amino acid include salts with aspartic acid, glutamic acid and the like.

The optically active β-hydroxy ester or a salt thereof obtained according to the present invention is useful as pharmaceuticals, agrichemicals, liquid crystals, and raw materials therefor.

EXAMPLE AND REFERENCE EXAMPLES

The following Examples and Reference Examples illustrate the present invention in more detail, but the present invention is not limited to them.

Nuclear magnetic resonance spectra ($^1$H-NMR) were measured using tetramethylsilane as an internal standard on JMTCO400/54 (400 MHz) manufactured by JEOL. Ltd., and δ values are reported in ppm.

Symbols used in Examples mean as follows: s: singlet, d: doublet, t: triplet, m: multiplet, br: broad, J: coupling constant, TFA: trifluoroacetic acid, $^t$Bu: tert-butyl, Tr: trityl.

Infrared absorption spectra (IR) were measured on Paragon 1000 manufactured by PerkinElmer, Inc.

Enantiomer excesses (% ee) were measured with high performance liquid chromatography. Columns for high performance liquid chromatography (CHIRALPAK AD, CHIRALCEL OD, CHIRALCEL OJ) were purchased from Dicel Chemical Industries Ltd.

Example 1 tert-butyl 3-hydroxy-4-methyl-3-(1-trityl-1H-imidazol-4-yl)pentanoate

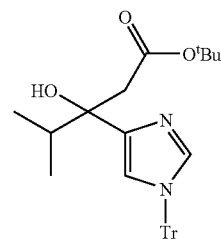

Under argon atmosphere, cinchonine (440 mg, 1.0 mmol) was suspended in tetrahydrofuran (absolute, 2.0 mL), and to this suspension was added a Reformatsky reagent (0.5 M; 8.0 mL, 4.0 mmol) dropwise under ice-cooling. After stirring for 10 minutes, pyridine (0.30 mL, 2 mmol) was added thereto dropwise. After stirring for 20 minutes under ice-cooling, the mixture was cooled to −40° C. A solution of 2-methyl-1-(1-trityl-1H-imidazol-4-yl)propan-1-one (1.0 mmol) in tetrahydrofuran (absolute, 4.0 mL) was added dropwise over 10 minutes, and the mixture was stirred at −40° C. for 4 hours. To this reaction solution was added 1N HCl (20 mL), which was then extracted with ethyl acetate (20 mL×2). The extracted solution was washed successively with an aqueous saturated sodium bicarbonate solution and an aqueous saturated sodium chloride solution. After the organic layer was dried with sodium sulfate, the solvent was removed under reduced pressure. The residue was analyzed with high performance liquid chromatography. Consequently, the yield was 73% and the enantiomer excess was 94%.

$^1$H NMR (400 MHz, CDCl$_3$) δ: 0.84 (3H, d, J=6.9 Hz), 0.88 (3H, d, J=6.9 Hz), 1.37 (9H, s), 1.94-2.05 (1H, m), 2.66 (1H, d, J=15.6 Hz), 3.01 (1H, d, J=15.6 Hz), 4.57 (1H, s), 6.79 (1H, s), 7.0-7.2 (6H, m), 7.2-7.4 (10H, m).

IR (KBr) vcm$^{-1}$: 3453, 2978, 1693, 1446, 1365, 1335, 1150, 951, 819, 749, 700.

High Performance Liquid Chromatography
Column: CHIRALPAK AD
Mobile phase: Hexane/Ethanol (95/5)
Flow rate: 0.5 mL/min.
Detection: TV (254 nm)
Temperature: Room Temperature
Retention Time: 35.4 minutes (enantiomer 15.6 minutes)

Example 2 tert-butyl 3-hydroxy-3-(1-trityl-1H-imidazol-4-yl)propionate

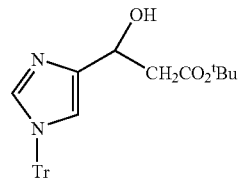

Under argon atmosphere, cinchonine (220 mg, 0.5 mmol) was suspended in tetrahydrofuran (absolute, 1.0 mL), and to this suspension was added a Reformatsky reagent (0.52 M; 7.7 mL, 1.51 mmol) dropwise under ice-cooling. After stirring for 10 minutes, pyridine (0.15 mL, 2 mmol) was added thereto dropwise. After stirring for 20 minutes under ice-cooling, the mixture was cooled to −40° C. A solution of 4-formyl-1-trityl-1H-imidazole (0.5 mmol) in tetrahydrofuran (absolute, 2.0 mL) was added dropwise over 10 minutes, and the mixture was stirred at −40° C. for 4 hours. To this reaction solution was added 1N HCl (10 mL), which was then extracted with ethyl acetate (10 mL×2). The extracted solution was washed successively with an aqueous saturated sodium bicarbonate solution and an aqueous saturated sodium chloride solution. After the organic layer was dried with sodium sulfate, the solvent was removed under reduced pressure. The residue was analyzed with high performance liquid chromatography. Consequently, the yield was 84% and the enantiomer excess was 66%.

$^1$H NMR (400 MHz, CDCl$_3$) δ: 1.42 (9H, s), 2.74 (1H, dd, J=16.4 and 7.8 Hz), 2.81 (1H, dd, J=16.4 and 4.6 Hz), 3.42 (1H, d, J=4.9 Hz), 5.06 (1H, m), 6.79 (1H, s), 7.1-7.2 (7H, m), 7.29-7.36 (8H, m), 7.37 (1H, d, J=1.4 Hz)

IR (KBr) vcm$^{-1}$: 3197, 2974, 1726, 1493, 1444, 1148, 701.

High Performance Liquid Chromatography
Column: CHIRALPAK AD
Mobile phase: Hexane/2-Propanol (90/10)
Flow rate: 1.0 mL/min.
Detection: UV (220 nm)
Temperature: 30° C.
Retention Time: 22.5 minutes (enantiomer 16.8 minutes)

Example 3 tert-butyl 3-hydroxy-3-phenyl-3-(pyridin-2-yl)propionate

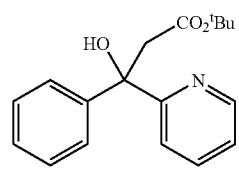

Under argon atmosphere, cinchonine (440 mg, 1.0 mmol) was suspended in tetrahydrofuran (absolute, 2.0 mL), and to this suspension was added a Reformatsky reagent (0.5 M; 8.0 mL, 4.0 mmol) dropwise under ice-cooling. After stirring for 10 minutes, pyridine (0.30 mL, 2 mmol) was added thereto dropwise. After stirring for 20 minutes under ice-cooling, the mixture was cooled to −40° C. A solution of 2-benzoylpyridine (183 mg, 1.0 mmol) in tetrahydrofuran (absolute, 4.0 mL) was added dropwise over 10 minutes, and the mixture was stirred at −40° C. for 4 hours. To this reaction solution was added 1N HCl (20 mL), which was then extracted with ethyl acetate (20 mL×2). The extracted solution was washed successively with an aqueous saturated sodium bicarbonate solution and an aqueous saturated sodium chloride solution. After the organic layer was dried with sodium sulfate, the solvent was removed under reduced pressure. The residue was analyzed with high performance liquid chromatography. Consequently, the yield was 98% and the enantiomer excess was 90%.

$^1$H NMR (400 MHz, CDCl$_3$) δ: 1.32 (9H, s), 3.12 (1H, d, J=15.8 Hz), 3.52 (1H, d, J=15.8 Hz), 5.51 (1H, s), 7.1-7.3 (4H, m), 7.5-7.7 (4H, m), 8.5 (1H, m).

IR (neat) vcm$^{-1}$: 3461, 2978, 1702, 1368, 1154, 700.

High Performance Liquid Chromatography
Column: CHIRALCEL OJ
Mobile phase: Hexane/Ethanol (975/25)
Flow rate: 1.0 mL/min.
Detection: UV (220 nm)
Temperature: 30° C.
Retention Time: 12.0 minutes (enantiomer 14.4 minutes)

Example 4 tert-butyl 3-hydroxy-3-(4-chlorophenyl)-3-(pyridin-2-yl)propionate

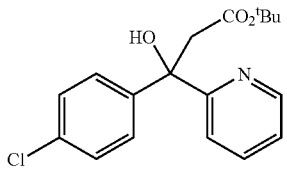

Under argon atmosphere, cinchonine (440 mg, 1.0 mmol) was suspended in tetrahydrofuran (absolute, 2.0 mL), and to this suspension was added a Reformatsky reagent (0.5 M; 8.0 mL, 4.0 mmol) dropwise under ice-cooling. After stirring for 10 minutes, pyridine (0.30 mL, 2 mmol) was added thereto dropwise. After stirring for 20 minutes under ice-cooling, the mixture was cooled to −400° C. A solution of 2-(4-chlorobenzoyl)pyridine (218mg, 1.0 mmol) in tetrahydrofuran (absolute, 4.0 mL) was added dropwise over 10 minutes, and the mixture was stirred at −40° C. for 4 hours. To this reaction solution was added 1N HCl (20 mL), which was then extracted with ethyl acetate (20 mL×2). The extracted solution was washed successively with an aqueous saturated sodium bicarbonate solution and an aqueous saturated sodium chloride solution. After the organic layer was dried with sodium sulfate, the solvent was removed under reduced pressure. The residue was analyzed with high performance liquid chromatography. Consequently, the yield was 81% and the enantiomer excess was 91%.

$^1$H NMR (400 MHz, CDCl$_3$) δ: 1.33 (9H, s), 3.08 (1H, d, J=16.0 Hz), 3.49 (1H, d, J=16.0 Hz), 5.52 (1H, s), 7.1-7.7 (7H, m), 8.4-8.6 (1H, m).

IR (KBr) vcm$^{-1}$: 3358, 2977, 1694, 1591, 1490, 1467, 1368, 1159, 1090, 1013, 830, 785, 755, 591.

High Performance Liquid Chromatography
Column: CHIRALCEL OJ
Mobile phase: Hexane/Ethanol/Trifluoroacetic acid (99/1/0.1)

Flow rate: 0.5 mL/min.
Detection: UV (254 nm)
Temperature: Room Temperature
Retention Time: 24.5 minutes (enantiomer 17.3 minutes)

Example 5 tert-butyl 3-hydroxy-3-(pyridin-2-yl)butanoate

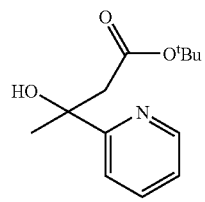

Under argon atmosphere, cinchonine (440 mg, 1.0 mmol) was suspended in tetrahydrofuran (absolute, 2.0 mL), and to this suspension was added a Reformatsky reagent (0.5 M; 8.0 mL, 4.0 mmol) dropwise under ice-cooling. After stirring for 10 minutes, pyridine (0.30 mL, 2 mmol) was added thereto dropwise. After stirring for 20 minutes under ice-cooling, the mixture was cooled to −40° C. A solution of 2-acetylpyridine (120 mg, 1.0 mmol) in tetrahydrofuran (absolute, 4.0 mL) was added dropwise over 10 minutes, and the mixture was stirred at −40° C. for 4 hours. To this reaction solution was added 1N HCl (20 mL), which was then extracted with ethyl acetate (20 mL×2). The extracted solution was washed successively with an aqueous saturated sodium bicarbonate solution and an aqueous saturated sodium chloride solution. After the organic layer was dried with sodium sulfate, the solvent was removed under reduced pressure. The residue was analyzed with high performance liquid chromatography. Consequently, the yield was 94% and the enantiomer excess was 86%.

$^1$H NMR (400 MHz, CDCl$_3$) δ: 1.30 (9H, s), 1.53 (3H, s), 2.73 (1H, d, J=15.5 Hz), 3.10 (1H, d, J=15.5 Hz), 4.95 (1H, s), 7.1 (1H, m), 7.6-7.7 (2H, m), 8.5 (1H, m).

IR (KBr) vcm$^{-1}$: 3477, 2979, 1704, 1591, 1472, 1434, 1392, 1368, 1228, 1159, 1107, 793, 751.

High Performance Liquid Chromatography
  Column: CHIRALPAK AD
  Mobile phase: Hexane/Ethanol (975/25)
  Flow rate: 0.5 mL/min.
  Detection: UV (220 nm)
  Temperature: Room Temperature
  Retention Time: 17.4 minutes (enantiomer 15.8 minutes)

Example 6 tert-butyl 3-hydroxy-3-(pyridin-2-yl)propionate

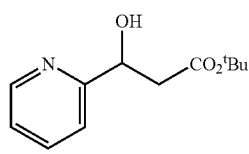

Under argon atmosphere, cinchonine (440 mg, 1.0 mmol) was suspended in tetrahydrofuran (absolute, 2.0 mL), and to this suspension was added a Reformatsky reagent (0.4 M; 10.0 mL, 4.0 mmol) dropwise under ice-cooling. After stirring for 10 minutes, pyridine (0.30 mL, 2 mmol) was added thereto dropwise. After stirring for 20 minutes under ice-cooling, the mixture was cooled to −40° C. A solution of 2-pyridinecarbaldehyde (108 mg, 1.0 mmol) in tetrahydrofuran (absolute, 4.0 mL) was added dropwise over 10 minutes, and the mixture was stirred at −40° C. for 4 hours. To this reaction solution was added 1N HCl (20 mL), which was then extracted with ethyl acetate (20 mL×2). The extracted solution was washed successively with an aqueous saturated sodium bicarbonate solution and an aqueous saturated sodium chloride solution. After the organic layer was dried with sodium sulfate, the solvent was removed under reduced pressure. The residue was analyzed with high performance liquid chromatography. Consequently, the yield was 94% and the enantiomer excess was 70%.

$^1$H NMR (400MHz, CDCl$_3$) δ: 1.44 (9H, s), 2.65-2.72 (1H, m), 2.81-2.87 (1H, m), 4.27 (1H, d, J=4.9 Hz), 5.13 (1H, m), 7.1-7.3(1H, m), 7.4 (1H, d, J=6.8 Hz), 7.6-7.8(1H, m), 8.54 (1H, d, J=3.0 Hz).

IR (neat) vcm$^{-1}$: 2979, 1727, 1594, 1368, 1152.

High Performance Liquid Chromatography
  Column: CHIRALPAK AD
  Mobile phase: Hexane/Ethanol (95/5)
  Flow rate: 1.0 mL/min.
  Detection: UV (220 nm)
  Temperature: 30° C.
  Retention Time: 20.1 minutes (enantiomer 18.0 minutes)

Industrial Applicability

According to the method of the present invention, optically active β-hydroxy esters or salts thereof which is useful as pharmaceuticals, agrichemicals, liquid crystals, and raw materials therefor can be obtained easily at high optical purities and, thus, the method is very useful industrially.

What we claim are:

1. A method for producing an optically active β-hydroxy ester compound represented by the general formula:

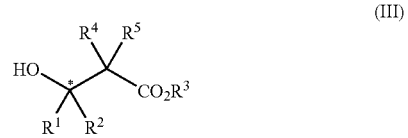

(III)

wherein
  $R^1$ represents a hydrogen atom or an optionally substituted aliphatic hydrocarbon group,
  $R^2$ represents a 5- or 6-membered nitrogen-containing heterocyclic group, which is represented by the general formula:

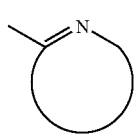 (V)

wherein the ring may be substituted, and may have one or more heteroatoms selected from the group consistinig of an oxygen atom, a sulfur atom and a nitrogen atom in addition to the nitrogen atom in the formula, and may have one or more double bonds in addition to the double bond in the formula; or the general formula:

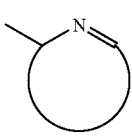 (VI)

wherein the ring may be substituted, and may have one or more heteroatoms selected from the group consisting of an oxygen atom, a sulfur atom and a nitrogen atom in addition to the nitrogen atom in the formula, and may have one or more double bonds in addition to the double bond in the formula, $R^3$ represents an optionally substituted hydrocarbon group, $R^4$ and $R^5$ are the same or different, and represent a hydrogen atom or an optionally substituted hydrocarbon group, or $R^4$ and $R^5$ may be taken together to form a ring, wherein said ring may be substituted, the symbol "*" represents an optically active center, or a salt thereof, which comprises reacting, in the presence of a cinchona alkaloid selected from the group consisting of cinchonine, cinchonidine, quinine and quinidine or a salt thereof, a compound represented by the general formula:

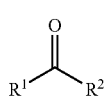 (I)

wherein $R^1$ and $R^2$ are as defined above or a salt thereof with a compound represented by the general formula:

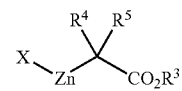 (II)

wherein $R^3$, $R^4$ and $R^5$ are as defined above, and X is a halogen atom, or a polymer thereof or a salt thereof.

2. The method according to claim 1, which further comprises adding a base.

3. The method according to claim 2, wherein the base is pyridine.

4. The method according to claim 1, wherein $R^2$ is an optionally substituted 2-pyridyl group or 4-imidazolyl group.

5. The method according to claim 1, wherein $R^2$ is a group represented by the general formula:

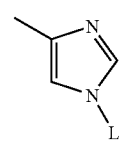 (IV)

wherein L represents a protecting group.

* * * * *